US006966923B2

(12) United States Patent
Gittings

(10) Patent No.: US 6,966,923 B2
(45) Date of Patent: Nov. 22, 2005

(54) STENT DELIVERY SYSTEM AND LOW PROFILE STENT

(75) Inventor: Darin C. Gittings, Sunnyvale, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 172 days.

(21) Appl. No.: 10/350,582

(22) Filed: Jan. 24, 2003

(65) Prior Publication Data

US 2004/0147997 A1   Jul. 29, 2004

(51) Int. Cl.[7] ............................................. A61F 2/06
(52) U.S. Cl. ...................................... 623/1.2; 623/1.15
(58) Field of Search ................................ 606/191, 198, 606/200; 623/1.15, 1.16, 1.17, 1.18, 1.19, 623/1.2

(56) References Cited

U.S. PATENT DOCUMENTS

| | | | |
|---|---|---|---|
| 5,375,612 A * | 12/1994 | Cottenceau et al. ........ 128/899 |
| 5,383,887 A | 1/1995 | Nadal | |
| 5,607,445 A | 3/1997 | Summers ..................... 606/198 |
| 5,746,766 A * | 5/1998 | Edoga .......................... 623/1.2 |
| 5,843,176 A * | 12/1998 | Weier .......................... 623/1.2 |
| 6,187,036 B1 * | 2/2001 | Shaolian et al. ............ 623/1.15 |
| 6,475,238 B1 * | 11/2002 | Fedida ........................ 623/1.16 |
| 6,565,597 B1 * | 5/2003 | Fearnot et al. .............. 623/1.14 |
| 6,764,503 B1 * | 7/2004 | Ishimaru ..................... 623/1.11 |

FOREIGN PATENT DOCUMENTS

| | | |
|---|---|---|
| EP | 0423 916 B1 | 4/1995 |
| WO | WO 01/06952 | 2/2001 |
| WO | WO 02/39888 A2 | 5/2002 |
| WO | WO 02/39888 A3 | 5/2002 |

* cited by examiner

*Primary Examiner*—Corrine McDermott
*Assistant Examiner*—Thomas J Sweet

(57) ABSTRACT

A stent and stent delivery system with a catheter and stent operably coupled to the catheter. The collapsible stent includes a first end region opposed to a second end region. A plurality of elongated elements is arranged in a generally zig-zag fashion between the end regions. A plurality of loops formed at an overlying intersection of adjacent elongated elements is positioned at each of the end regions. The tips of the plurality of loops in the first end region form a first end circle. The loops are arranged in a twist formation when the stent is in the collapsed configuration. The twist formation includes each of the loops being oriented at a twist angle measured in a first end plane defined by the first end circle between a line tangent to the first end circle perpendicular to a radius line from the longitudinal axis of the stent to a tip of the individual loop being measured, and a loop line longitudinally dividing the individual loop.

41 Claims, 6 Drawing Sheets

STENT DELIVERY SYSTEM AND LOW PROFILE STENT

TECHNICAL FIELD OF THE INVENTION

The technical field of this disclosure is medical implant devices, particularly, a low profile stent and stent delivery system.

BACKGROUND OF THE INVENTION

Balloon angioplasty has been used for the treatment of narrowed and occluded blood vessels. A frequent complication associated with the procedure is restenosis, or vessel re-narrowing. Within 3–6 months of angioplasty, restenosis occurs in almost 50 percent of patients. To reduce the incidence of re-narrowing, several strategies have been developed. Implantable prosthetic devices, such as stents, have been used to reduce the rate of angioplasty related restenosis by about half. The use of such prosthetic devices has greatly improved the prognosis of these patients.

The objective in angioplasty is to enlarge the lumen of the affected coronary artery by radial hydraulic expansion. This is generally accomplished by inflating a balloon within the narrowed lumen of the affected artery. Radial expansion of the coronary artery may occur in several different dimensions, and is related to the nature of the plaque. Soft, fatty plaque deposits are flattened by the balloon, while hardened deposits are cracked and split to enlarge the lumen. The wall of the artery itself may also be stretched as the balloon is inflated. With simple angioplasty, the balloon may be threaded through the artery with a catheter and inflated at the place where the blood vessel is blocked. After the procedure, the balloon is then removed. The stent may then be used to support open the artery and may be deployed along with the balloon or after the balloon is removed. The use of a stent may reduce the risk of restenosis to 20–30 percent.

The stent may be formed from a generally tubular body that can be expanded from a collapsed configuration into a deployed configuration. The stent body may include a plurality of elongated element lengths (e.g., wire lengths, or the like) that are connected together to permit the body to be expanded. The stent may be coupled to a deployment system (e.g., a catheter) in a collapsed configuration. For example, the stent may be compressed within a lumen formed within a catheter or onto a catheter balloon. The catheter including the stent may be then advanced endovascularly (or within another vessel type) to the afflicted region of the body passage. While fed through the vessel, the stent remains in the collapsed configuration.

Once the stent has reached the afflicted region in the body passage, it may be expanded (radially) outward into the deployed configuration. The stent may be expanded into its deployed configuration by inflating the catheter balloon so that expansion of the stent is achieved in sympathy with the inflation of the balloon. Alternatively, the stent may be manufactured from a resilient material such that when it is collapsed, the stent may naturally expand from a "tense" collapsed configuration into a "relaxed" deployed configuration. In such a case, the stent self-expands as it is forced from the catheter lumen.

Given that the deployment system must typically accommodate the collapsed stent, a reduced collapsed profile size may equate to a reduced size in its coupled deployment system. As such, numerous benefits may be provided by a reduction in stent and (potentially) deployment system size. For example, as the stent is advanced to the site of deployment, it may encounter a sometimes tortuous and narrow network of vessels. Smaller sized stents and deployment systems may facilitate easier negotiation of such vessel networks. Other benefits of minimizing the deployment system may include less disruption of an atheroma and plaque that could lead to emboli, less disruption of blood flow, less likelihood of vessel wall damage, and reduced vessel puncture size for intraluminal access. Accordingly, it would be desirable to minimize the stent collapsed profile size.

U.S. Pat. No. 5,383,887 to Nadal, entitled Device for Selectively Forming a Temporary Blood Filter, describes device which can be implanted inside a vessel to form a blood filter, the device having a structure that can be expanded or compressed such that, in its expanded position, it can contact the interior of a vessel. The device includes loops for variably constricting the structure, but does not disclose loops to minimize the collapsed profile size.

PCT Publication WO 01/06952 to Fearnot, et al., entitled Stent Adapted for Tangle Free Deployment, describes an expandable stent prosthesis in which the apices of the bends located at least one end of the stent are individually twisted at an angle to the circumference of the stent to form a fan blade-like arrangement to reduce the likelihood of entanglement during deployment. The expandable stent prosthesis includes struts united at an apex with a hairpin, simple bend, or 'safety pin' turn in which the struts are substantially parallel in the compressed condition, but does not disclose crossing the struts to form loops.

Therefore, it is desirable to provide a stent delivery system and low profile stent that overcomes the aforementioned and other disadvantages.

SUMMARY OF THE INVENTION

One aspect of the present invention provides a stent having a deployed configuration and a collapsed configuration. The stent includes a first end region opposed to a second end region. A plurality of elongated elements is arranged in a generally zig-zag fashion between the end regions. A plurality of loops formed at an overlying intersection of adjacent elongated elements is positioned at each of the end regions. The tips of the plurality of loops in the first end region form a first end circle. The loops are arranged in a twist formation when the stent is in the collapsed configuration. The twist formation includes each of the loops being oriented at a twist angle measured in a first end plane defined by the first end circle between a tangent line tangent to the first end circle and a loop line longitudinally dividing the individual loop. A graft material may be disposed on the stent.

Another aspect of the invention provides a stent delivery system. The system includes a stent operably coupled to a catheter. The stent may include the features described above.

DETAILED DESCRIPTION

Figure 1:
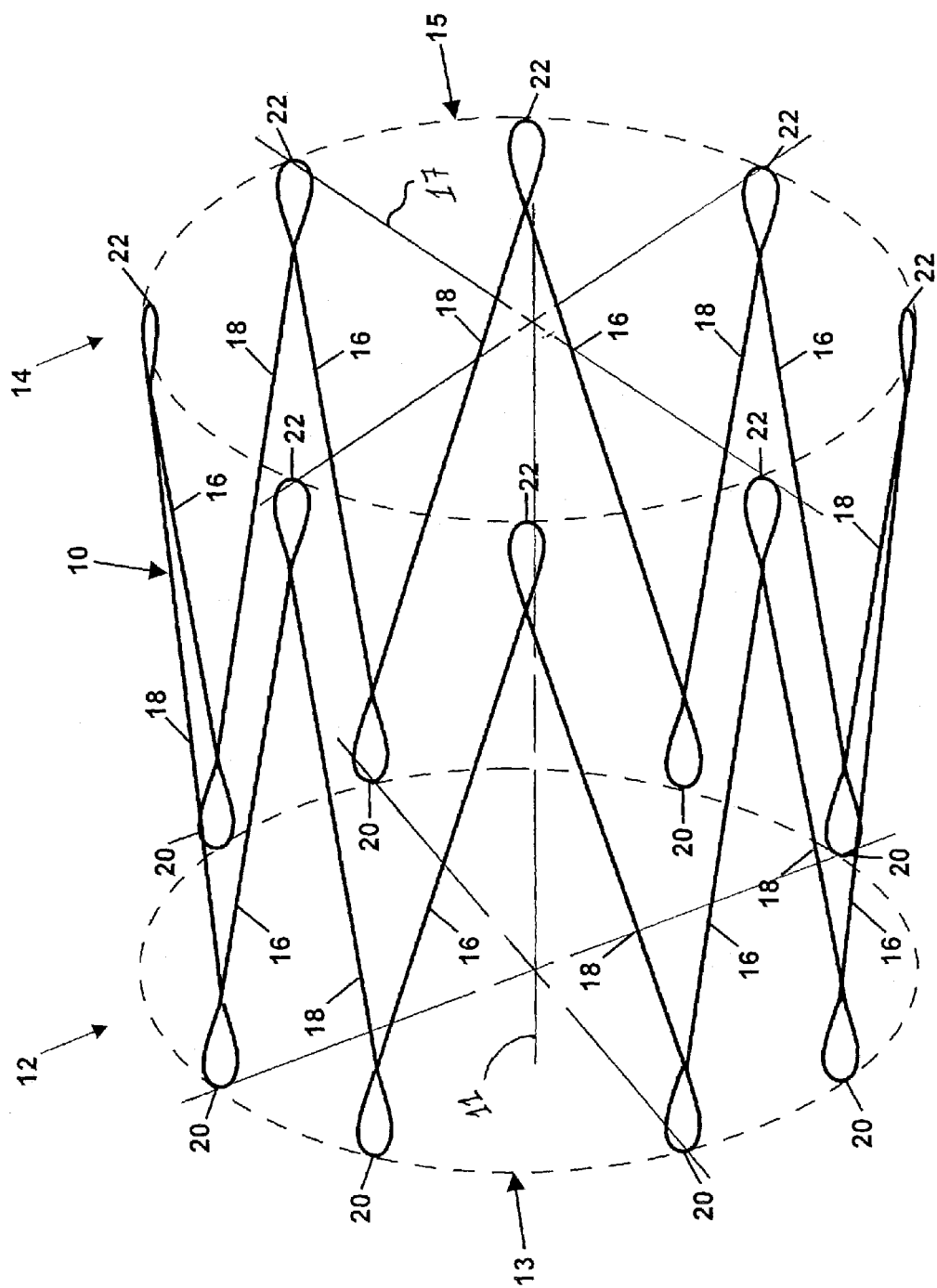
FIG. 1 is a side perspective view of a stent according to the invention, the stent shown in a deployed configuration.

Referring to the drawings, FIG. 1 shows a side perspective view of a tubular stent according to the invention and shown generally by reference numeral 10. Stent 10 is shown in a deployed configuration. Stent 10 includes a first end region 12 opposed to a second end region 14, as generally indicated by the reference numerals. A plurality of elongated elements 16, 18, in this case sixteen elongated elements, are arranged in a generally zig-zag fashion between the opposed first end region 12 and the second end region 14. A plurality of loops 20, in this case eight loops, are positioned at the first end region 12 and a plurality of loops 22 in this case eight loops, are positioned at the second end region 14. The loops 20, 22 connect the elongated elements 16 to the elongated elements 18. The points at the extreme ends of the tips of the loops 20 generally form a first end (imaginary) circle 13, which defines a first end plane (not shown) and the points at the extreme ends of the tips of the loops 22 generally form a second end (imaginary) circle 15, which defines a second end plane (not shown). The shape of the stent defines a longitudinal axis 11 of the stent with a typical radius 17 from the centerline at the longitudinal axis 11 to a tip of an individual loop (the tip 23 is discuss with respect to FIG. 2). Those skilled in the art will recognize that the number of elongated elements and loops may vary from that described and that shapes other than circles, such as ellipses or ovals, may be formed by the arrangement of the points at the extreme end of the tips of the loops 20 ("tips" is used primarily to designate the points at the extreme end of the tips of the loops). Further, the size formed by the arrangement of points may vary from end to end, and one end of the structure may contain loops, while the other end may contain a conventional corner (or Z-shaped) bend.

The elongated elements 16, 18 may extend generally linearly between opposed loops 20, 22. The stent 10 may be formed by bending a continuous elongated element to define the loops 20, 22 and the elongated elements 16, 18 extending therebetween. The continuous elongated element may be manufactured from wide variety of materials such as stainless steel, nitinol, MP35N, tantalum, glass, ceramic, nickel, titanium, aluminum, polymeric materials, resilient materials, alloys, or combinations thereof. The stent 10 may be welded, molded, or consist of filaments or fibers which are wound or braided together in order to form the continuous elongated element. As known in the art and further discussed below, the stent 10 may be self-expanding or balloon expanded.

Figure 2:
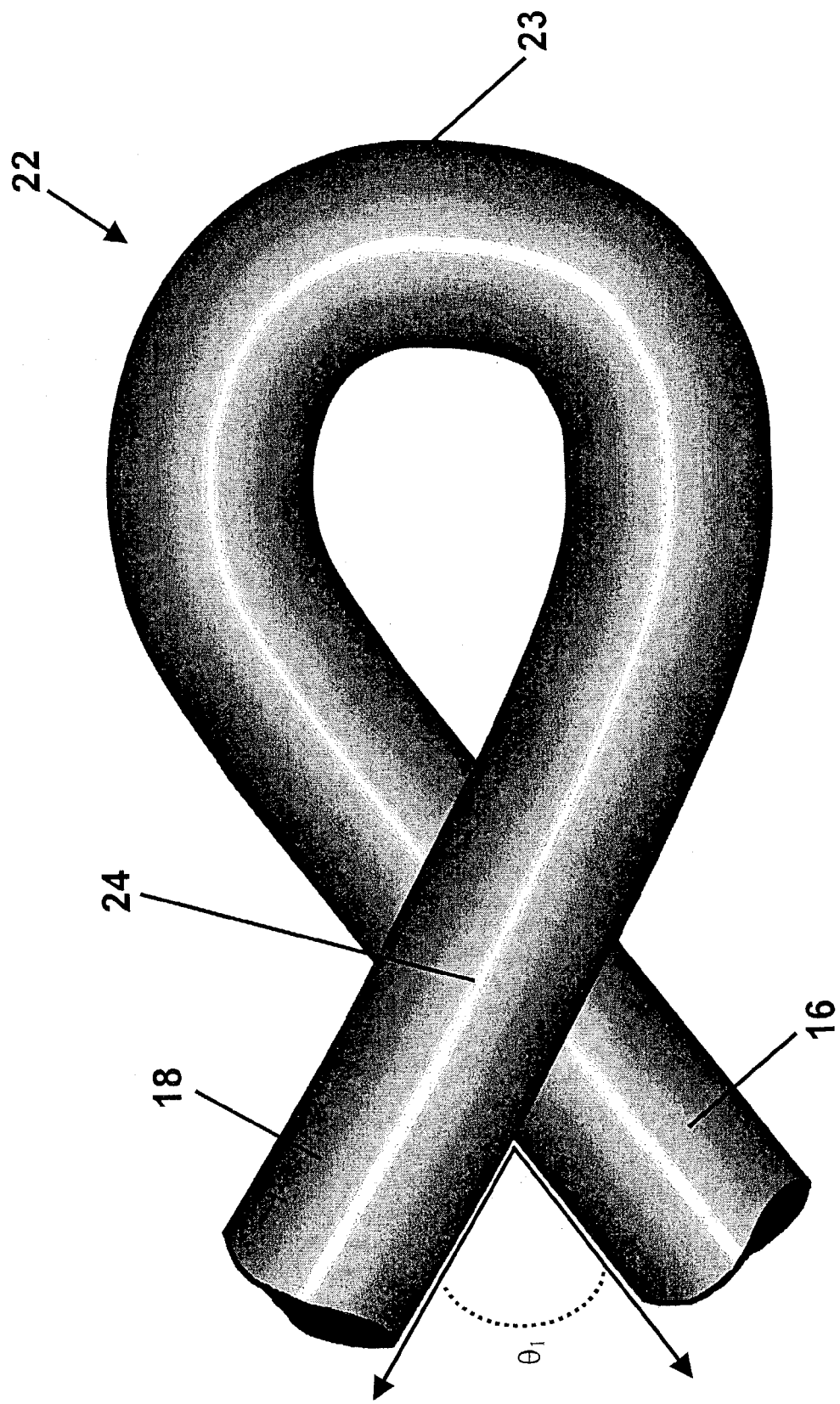
FIG. 2 is a close-up view of a loop of the stent of FIG. 1.

Referring now to FIG. 2 a detailed view of the loop 22 is provided. The view is from a center (longitudinal axis) of the stent along a radius of the second end (imaginary) circle (not shown). The loops 20 may have a similar configuration to the example illustrated for loops 22. The loop 22 is formed at an overlying intersection 24 of adjacent elongated elements 16, 18. The loop 22 may be formed whereby the strand of material forming the elongated element 18 extends on to wrap around and under itself eventually forming the loop and then continuing on as the elongated element 16. At the point of the overlying intersection 24, the adjacent elongated elements 16, 18 may physically contact one another during collapse, deployment, and/or operation of the stent.

Loop angle $\theta_1$ is defined by the angle between the projection of elongated element 16 and adjacent elongated element 18 on a plane perpendicular to the radius of the second end circle (not shown) and containing the tip 23 of the loop 22. The loop 22 may be an elastic structure, which may allow some bend and twist (i.e., brought on by mechanical stresses placed on the stent). As such, the loop angle $\theta_1$ may change during collapse, deployment, and operation of the stent. Those skilled in the art will recognize that the degree of the loop angle $\theta_1$ may vary and depend on such factors as the number of elongated elements and loops, the elongated element length, resiliency of the stent material, the degree of stent collapse, mechanical stress placed on the stent, and the like. In one embodiment, the loop angle $\theta_1$ may vary from about 1 to 60 degrees, depending on the aforementioned factors. In another embodiment, the loop angle $\theta_1$ may vary from about 1 to 90 degrees or more.

Figure 3B:
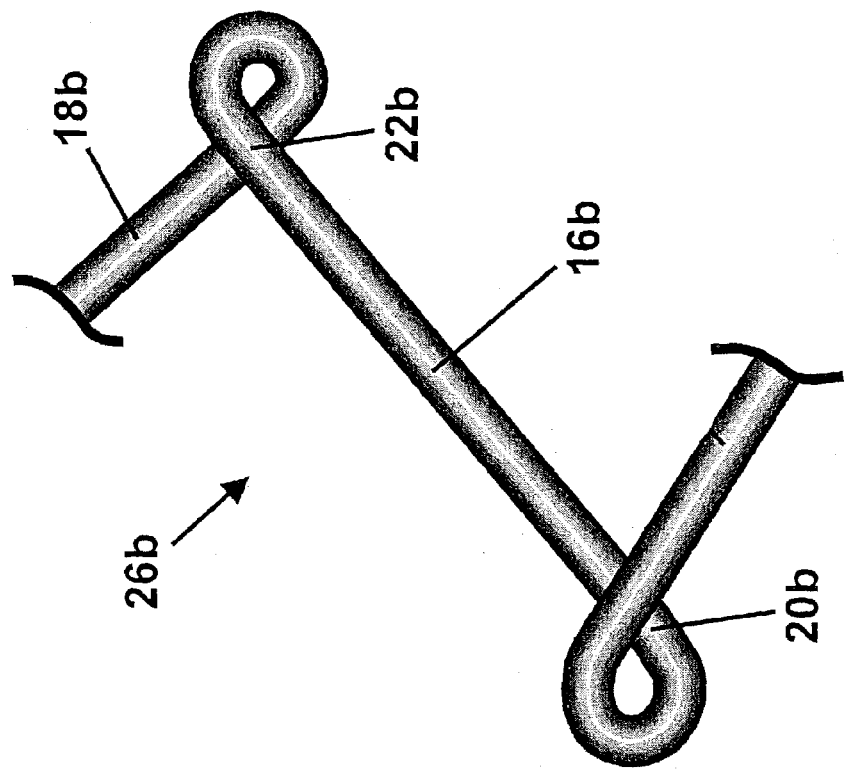
FIGS. 3A and 3B are detailed views of two loop-elongated element configurations.
Figure 3A:
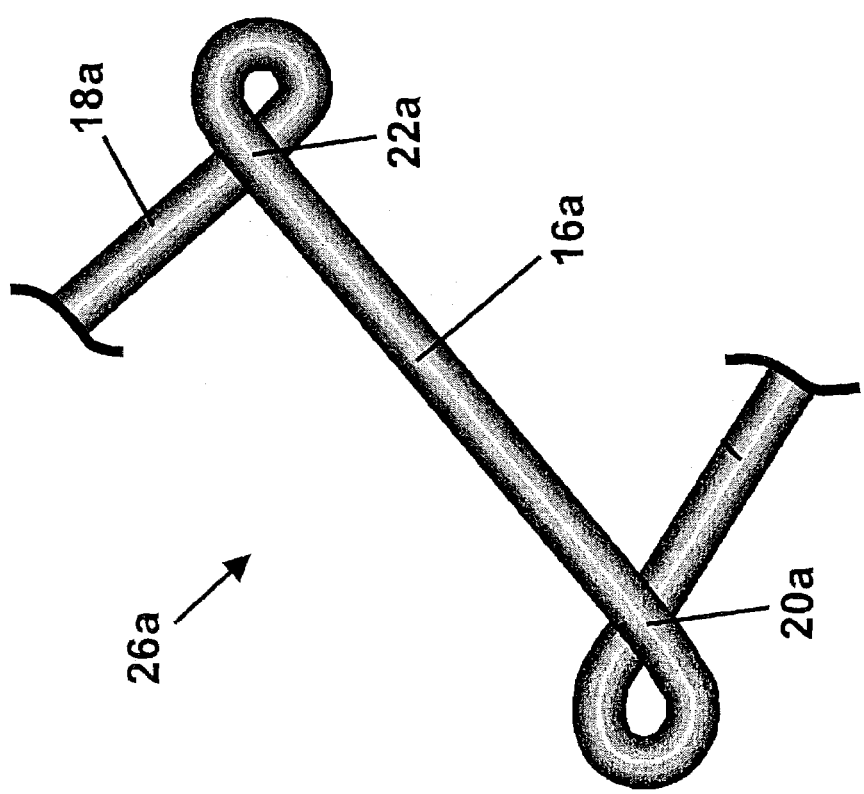

FIGS. 3A and 3B are detailed views of two loop-elongated element configurations 26a, 26b. As shown in FIG. 3A, elongated element 16a extends from a first intersection side 22a to another first (same) intersection side 20a. This is referred to herein as a "same-sided" configuration. The "same-sided" configuration, although feasible, may provide a collapsed profile size for the stent which is larger than optimum. In one embodiment according the invention, as shown in FIG. 3B, elongated element 16b extends from a first intersection side 22b to a second (opposed) intersection side 20b. This is referred to herein as an "over-under" configuration. The "over-under" configuration is generally optimum as it allows the stent to be collapsed radially to a relatively small profile size.

Figure 4B:
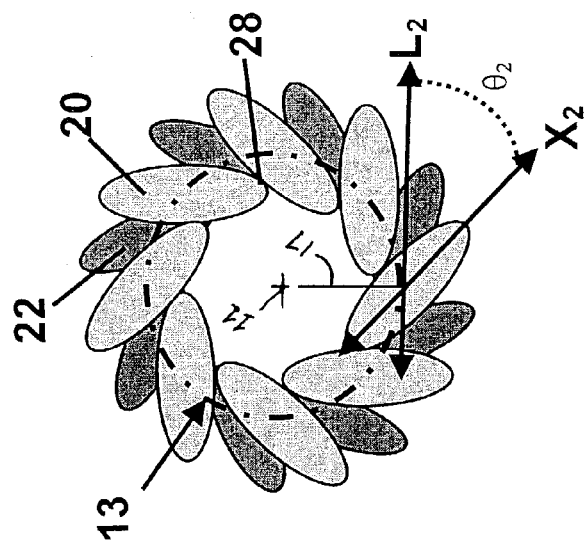
FIG. 4B is an end view of the stent shown in a collapsed configuration.
Figure 4A:
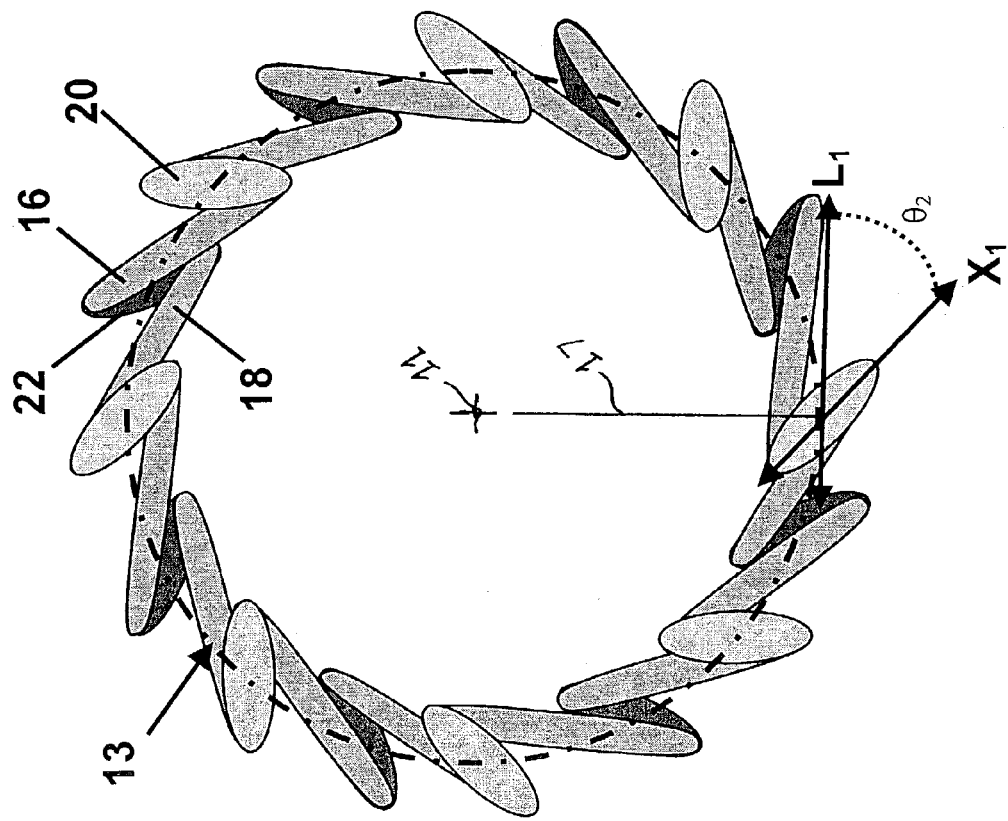
FIG. 4A is an end view of a portion of the stent shown in a deployed configuration.

FIGS. 4A and 4B show end views of the first end region of the stent in a deployed configuration and collapsed configuration, respectively. The second end region may be similar, but is not necessarily similar. The loops 20, 22 are arranged in a twist formation when the stent is in the collapsed configuration. The loops 20, 22 may also be arranged in the twist formation when the stent is in the deployed configuration. In another embodiment, the loops 20, 22 may depart from the twist formation when the stent is in the deployed configuration, i.e., the loops 20, 22 may open when deployed so that they are no longer strictly loops.

The twist formation may be illustrated by the end views provided in FIGS. 4A and 4B. Referring to the deployed configuration shown in FIG. 4A, the twist formation includes the loops 20, 22 oriented at an approximate twist angle $\theta_2$ between tangent line $L_1$ and loop line $X_1$. The tangent line $L_1$ is tangent to the first end circle 13 (perpendicular to the radius line 17 between the centered longitudinal axis 11 and the tip 23 of the individual loop whose twist angle is being assessed) and lies in the first end plane defined by the first end circle 13. The loop line $X_1$ divides the longitudinal projection of the end view of the loop 20 and lies in the first end plane. The twist angle of each individual loop is measured in a first end plane defined by the first end circle 15 between a line tangent $L_1$ to the first end circle 15 and intersecting a tip (e.g., 23) of the individual loop being measured and the loop line $X_1$ longitudinally dividing the individual loop in the first end region 12. Referring to the collapsed configuration shown in FIG. 4B, the twist formation includes the loops 20, 22 oriented at an approximate twist angle $\theta_2$ between tangent line $L_2$ and loop line $X_2$. FIG. 4B does not show elongated elements 16, 18 for clarity. The tangent line $L_2$ is tangent to the first end circle 13 and lies in the first end plane defined by the first end circle 13. The loop line $X_2$ divides the longitudinal projection of the end view of the loop 20 and lies in the first end plane.

Those skilled in the art will recognize that each loop need not assume the same exact twist angle and that many advantages of the present invention will be realized even with angle variation from loop to loop. In addition, the twist angle may vary based upon the given configuration of the stent, e.g., collapsed, deployed, or between, as well as on other factors. In one embodiment, the twist angle $\theta_2$ may be about 45 degrees, and may vary depending on the degree of collapse or deployment. In another embodiment, the loop angle $\theta_1$ may range from about 5 to 85 degrees.

For certain twist angles, adjacent loops may be in physical contact with one another when the stent is collapsed: an example is shown by reference numeral 28. In addition, the loops 20, 22 may allow the elongated elements 16, 18 (not shown) to move into a configuration in which the elongated elements are arranged in close proximity to one another as the stent is collapsed. The loop angle $\theta_1$ may be reduced as the stent is collapsed, so that the elongated elements 16, 18 are nearly parallel one another. The packing of the stent, i.e., the axial cross section in the collapsed condition, depends on the twist angle $\theta_2$, contact of the adjacent loops, and reduction of the loop angle $\theta_1$. The twist angle $\theta_2$ and the loop angle $\theta_1$ may be varied to provide optimal packing of the stent. The particular angles, as previously discussed, may depend on various factors and disclosed values are merely exemplary.

A stent and a stent-graft prosthesis made in accordance with the present invention may provide an excellent expansion ratio and ability to collapse into a relatively small deployment system. Numerous advantages are provided by the relatively small size required to accommodate the collapsed stent. One advantage of using a smaller deployment system relates to a reduced vessel puncture size for intraluminal deployment system access. For example, if the deployment system can be sufficiently small for placement of endovascular stent-grafts, a usual femoral artery cutdown procedure may be replaced by percutaneous entry, involving reduced trauma to the patient. Other potential advantages to downsizing the delivery system include less disruption of the atheroma and plaque that could lead to emboli, less disruption of blood flow, less likelihood of vessel wall damage, and easier navigation of vessel passageways.

Figure 5:
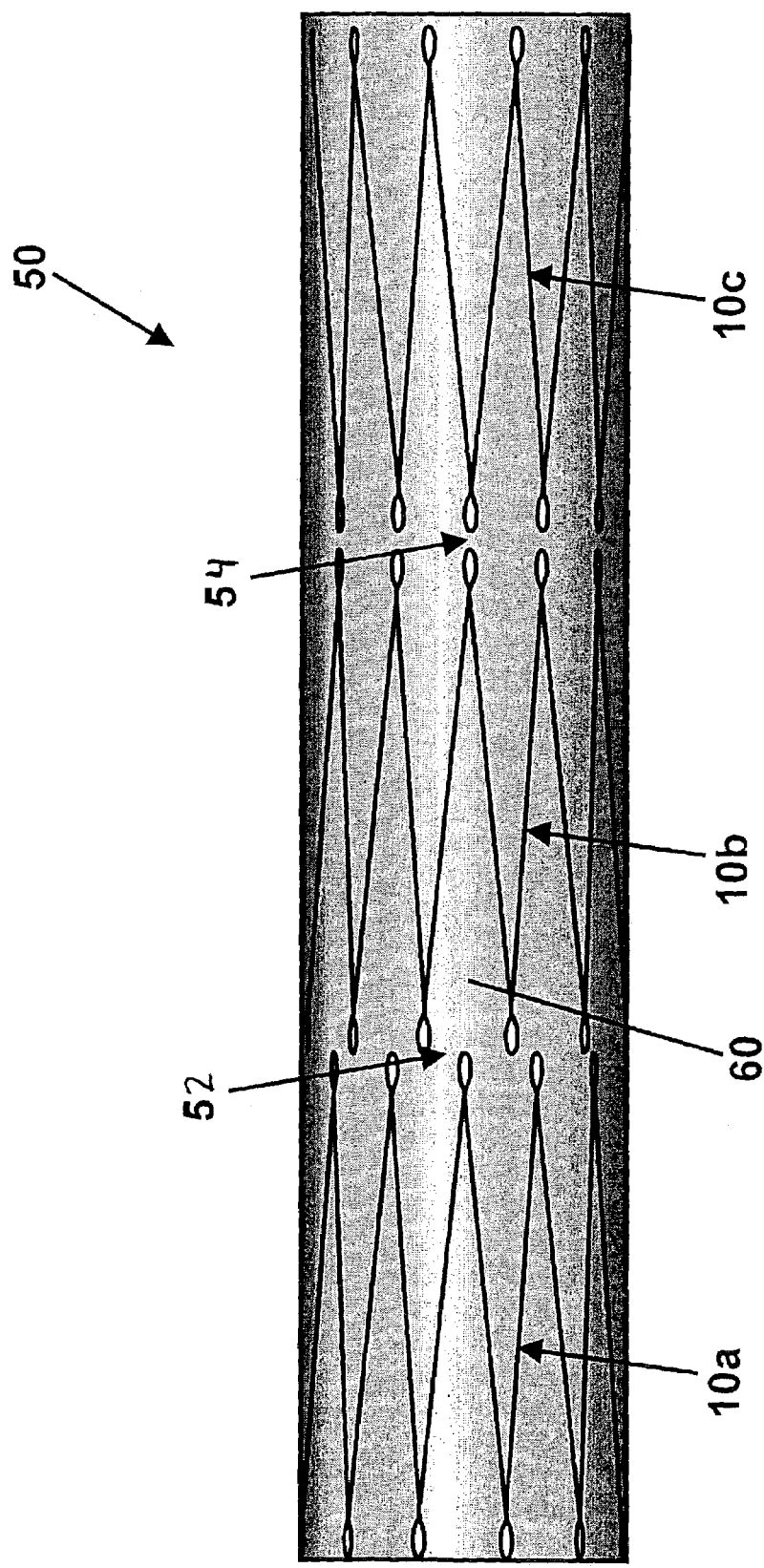
FIG. 5 is a side view of a stent including graft material according to the present invention.

Referring now to FIG. 5, a stent 50 including optional graft material 60 according to the present invention is shown. Stent 50 includes, in this case three, at least one stent elements 10a, 10b, and 10c, any of which is described above. Multiple stent elements 10a, 10b, and 10c may be arranged in series end-to-end to form the stent 50. Furthermore, loops of adjacent stent elements 10a, 10b, and 10c may be staggered as indicated at 52 or positioned end-to-end as indicated at 54. Those skilled in the art will recognize that where multiple stent elements are used to form the stent, the elements may be positioned in numerous configurations relative to one another.

The stent elements 10a, 10b, and 10c may be formed from a single continuous elongated element and/or attached to each other using a number of strategies. In one embodiment, multiple stent elements 10a, 10b, and 10c may be attached to one another by welding, adhesive bonding, and/or suturing. In another embodiment, the stent elements 10a, 10b, and 10c may be separate, but formed into a single stent 50 unit by virtue of their attachment to the graft material 60. Those skilled in the art will recognize that numerous strategies may be used to attach multiple stent elements one to another.

The graft material 60 may be disposed on an inner surface of the stent 50 thereby providing a stent-graft prosthesis. Alternatively, or in addition, the graft material may be disposed on an outer surface of the stent 50. The graft material 60 may be attached to the stent 50 using a number of strategies such as suturing, adhesive bonding, heat welding, ultrasonic welding, and the like. Where graft material is disposed on both the inner and outer surfaces, the stent may be sandwiched between and held in place by attaching the graft material layers to each other. The graft material 60 may be manufactured from any number of biocompatible membranes known in the art, such as polyester, polyethylene, polytetrafluoroethylene (PFTE), polyurethane, propylene, nylon, and the like.

The stent 50 may include at least one coating carrying a therapeutic agent, which can be applied to the stent 50 by dipping or spraying with a coating liquid, or applying the coating liquid with a combination of methods or other methods known to those of ordinary skill in the art. The coating may be applied as a liquid containing the drug or other therapeutic agent dispersed in a polymer/solvent matrix. In another embodiment, the therapeutic agent can be omitted from the coating and the coating included for its mechanical properties. The drug or therapeutic agent carried by the polymer of the coating may be varied depending on the body lumen involved, the result desired, and the therapy indicated. Combinations of therapeutic agents can be used. Examples of therapeutic agents that may be used in the coating include thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, anti-platelet agents, antimitotics, microtubule inhibitors, anti-secretory agents, actin inhibitors, remodeling inhibitors, antisense nucleotides, anti metabolites, antiproliferatives, anticancer chemotherapeutic agents, anti-inflammatory steroid or nonsteroidal anti-inflammatory agents, immunosuppressive agents, growth hormone antagonists, growth factors, dopamine agonists, radiotherapeutic agents, peptides, proteins, enzymes, extracellular matrix components, inhibitors, free radical scavengers, chelators, antioxidants, anti-polymerases, antiviral agents, photodynamic therapy agents, and gene therapy agents.

Figure 6:
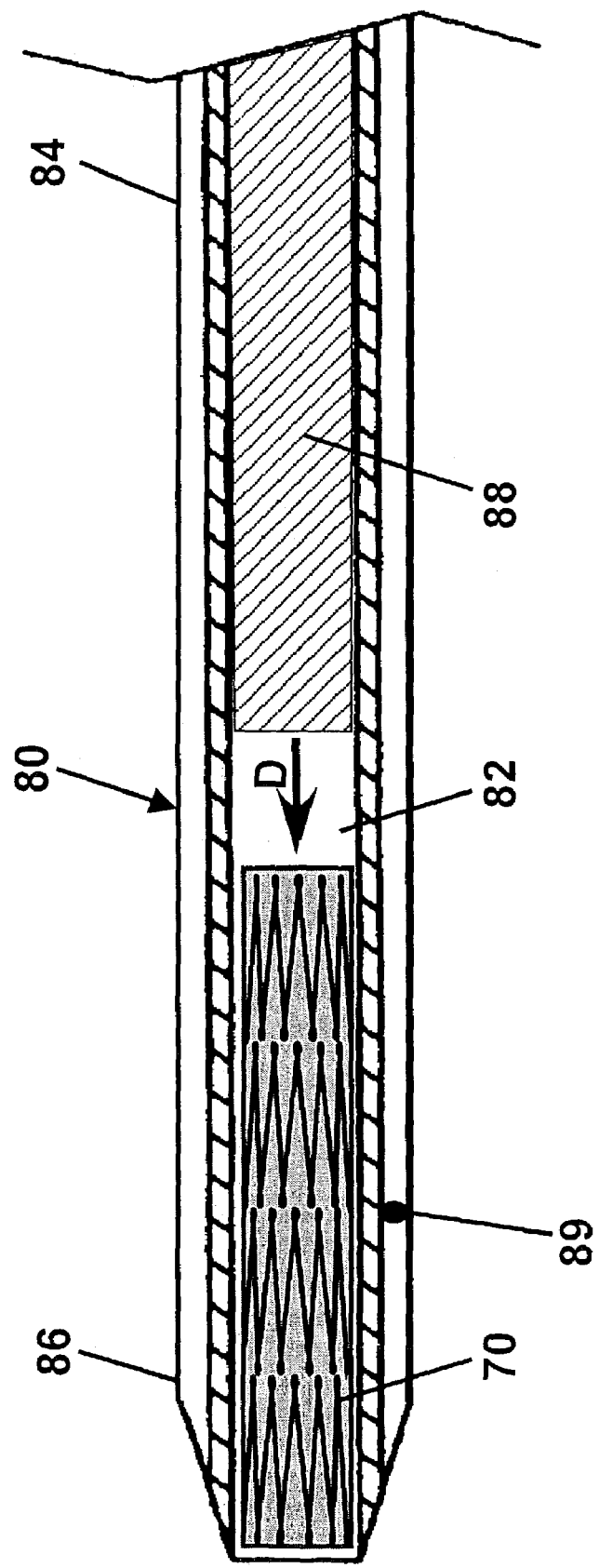
FIG. 6 is schematic cross sectional view of a stent-graft being in the process of being deployed from a catheter, in accordance with the present invention.

Referring now to FIG. 6, a stent-graft prosthesis 70 including four stents is shown being deployed from a catheter 80. Catheter 80 may include a lumen 82 formed therein. Catheter 80 may be manufactured from a flexible material with high lubricity to minimize sliding friction between the catheter 80 and prosthesis 70. Adequate catheter 80 materials may include polytetrafluoroethylene (PTFE), high-density polyethylene (HDPE), and the like. The inside surface of the catheter 80 may be coated with a lubricity enhancing compound or coating, such as PhotoLink® lubricity coating made by SurModics, Inc., to further decrease the friction between sliding surfaces.

The catheter lumen 82 may extend through catheter 80 axially from a proximal end 84 to a distal end 86 providing means for deploying the prosthesis 70. Catheter 80 may include a pushrod 88 slidably position within lumen 82 to deploy the prosthesis 70. At least one marker 89 may be disposed on catheter 80 to allow in situ visualization. In one embodiment, marker 89 may be manufactured from a number of materials used for visualization in the art including radiopaque materials platinum, gold, tungsten, metal, metal alloy, and the like. Marker 89 may be visualized by fluoroscopy, ultrasound, and other methods known in the art.

The small profile size of the collapsed stent-graft prosthesis 70 may allow minimization of the lumen 82 and catheter 80 sizes. Furthermore, prosthesis 70, catheter 80, and lumen 82 may vary in geometry, size, and configuration to suit a given application. Those skilled in the art will recognize that a wide variety of catheter 80 structures, including those capable of performing additional functions not described herein, may be readily adapted for use with the present invention. For example, catheter 80 may include a balloon coupled to inflation lumen and/or a delivery lumen with distal openings for substance delivery (e.g., therapeutic agents, contrast media, saline, fluids, and the like).

As shown in FIG. 6, prosthesis 70 may be collapsed to allow insertion within the catheter lumen 82 or to allow deployment with another adequate delivery device as known in the art. In another embodiment, the prosthesis may be collapsed and disposed on an expandable balloon catheter for deployment. Catheter 80 may then be positioned to an appropriate deployment site (e.g., a blood vessel undergoing PTCA treatment). Catheter 80 position may be monitored by visualization methods known in the art, such as fluoroscopy and/or intravascular ultrasound (IVUS). In one embodiment, radiopaque markers disposed on portion of the catheter 80 may be visualized by fluoroscopy.

After appropriate catheter 80 positioning, prosthesis 70 may be deployed. In one embodiment, the push rod 88 may be slidably advanced through the catheter lumen 82 until contact is made with the prosthesis 70, as indicated by arrow, D. The push rod 88 may be maintained in the fixed contact position with the prosthesis 70 as catheter 80 is withdrawn axially. The prosthesis 70 (stent) may self-expand radially outward (and optionally axially) as it emerges from the lumen 82 at the catheter distal end 86. If the prosthesis 70 stent is manufactured from a resilient material, the prosthesis 70 may self-expand due to the natural tendency of the material to expand to its "relaxed" configuration. In another embodiment, a balloon of a balloon-catheter may be inflated to expand the prosthesis 70 (stent). The prosthesis 70 may self-expand or balloon-expand to its deployed configuration. The prosthesis 70 may be expanded into engagement with a vessel wall. It is important to note that the stent of the prosthesis 70 may be deployed (without graft material) in a manner as described above.

While the embodiments according to the present invention disclosed herein may be presently considered preferred, various changes and modifications can be made without departing from the spirit and scope of the invention.

I claim:

1. A stent comprising:
   a first end region at a first longitudinal end of the stent opposed to a second end region at a second longitudinal end of the stent;
   elongated elements arranged in a generally zig-zag fashion between the first end region and the second end region; and
   a plurality of loops, each of the plurality of loops formed at an overlying intersection of adjacent elongated elements, each of the plurality of loops having a tip;
   wherein the tips of the plurality of loops in the first end region form a first end circle, and each individual loop in the first end region is arranged at a twist angle, the twist angle of each individual loop being measured in a first end plane defined by the first end circle between a line tangent to the first end circle perpendicular to a radius line from a longitudinal axis of the stent to a tip of the individual loop being measured and a loop line longitudinally dividing the individual loop in the first end region; and
   wherein the twist angle of each individual loop is a first twist angle when the stent is in a collapsed configuration and a second twist angle different from said first twist angle when the stent is in a deployed configuration.

2. The stent of claim 1 wherein the second twist angle is about 45 degrees.

3. The stent of claim 1 wherein the first twist angle is between about 5 to 85 degrees.

4. The stent of claim 1 wherein the tips of the plurality of loops in the second end region form a second end circle, and each individual loop in the second end region is arranged at a twist angle, the twist angle of each individual loop being measured in a second end plane defined by the second end circle between a line tangent to the second end circle perpendicular to a radius line from a longitudinal axis of the stent to a tip of the individual loop being measured and a loop line longitudinally dividing the individual loop in the second end region.

5. The stent of claim 4 wherein the overlying intersections for each of the elongated elements are in a same-sided configuration.

6. The stent of claim 4 wherein the overlying intersections for each of the elongated elements are in a over-under configuration.

7. The stent of claim 1 wherein the elongated elements extend generally linearly between opposed loops.

8. The stent of claim 1 wherein the plurality of loops in the first end region is arranged so that one loop contacts an adjacent loop when the stent is in a collapsed configuration.

9. The stent of claim 1 wherein the elongated elements are in physical contact at the overlying intersection of adjacent elongated elements.

10. The stent of claim 1 wherein the stent is self-expanding.

11. The stent of claim 10 wherein the stent is manufactured from a resilient material.

12. The stent of claim 1 wherein the stent is balloon-expandable.

13. The stent of claim 1 wherein the stent is formed by bending a continuous elongated element to define the loops and the elongated elements extending therebetween.

14. The stent of claim 1 further comprising a graft material disposed on the stent.

15. A stent delivery system comprising:
   a catheter; and
   a stent operably coupled to the catheter, the stent having a first end region at a first longitudinal end of said stent opposed to a second end region at a second longitudinal end of said stent; elongated elements arranged in a generally zig-zag fashion between the first end region and the second end region; and a plurality of loops, each of the plurality of loops formed at an overlying intersection of adjacent elongated elements, each of the plurality of loops having a tip;
   wherein the tips of the plurality of loops in the first end region form a first end circle, and each individual loop in the first end region is arranged at a twist angle, the twist angle of each individual loop measured in a first end plane defined by the first end circle between a line tangent to the first end circle perpendicular to a radius line from a longitudinal axis of the stent to a tip of the individual loop being measured and a loop line longitudinally dividing the individual loop in the first end region; and wherein the twist angle of each individual loop is a first twist angle when the stent is in a collapsed configuration and a second twist angle different from said first twist angle when the stent is in a deployed configuration.

16. The system of claim 15 wherein the tips of the plurality of loops in the second end region form a second end circle, and each individual loop in the second end region is arranged at a twist angle, the twist angle of each individual loop measured in a second end plane defined by the second end circle between a line tangent to the second end circle perpendicular to a radius line from a longitudinal axis of the stent to a tip of the individual loop being measured and a loop line longitudinally dividing the individual loop in the second end region.

17. The system of claim 16 wherein the overlying intersections for each of the elongated elements are in a same-sided configuration.

18. The system of claim 16 wherein the overlying intersections for each of the elongated elements are in a over-under configuration.

19. The system of claim 15 wherein the elongated elements extend generally linearly between opposed loops.

20. The system of claim 15 wherein the plurality of loops in the first end region is arranged so that one loop contacts an adjacent loop when the stent is in a collapsed configuration.

21. The system of claim 15 wherein the elongated elements are in physical contact at the overlying intersection of adjacent elongated elements.

22. The system of claim 15 wherein the stent is self-expanding.

23. The system of claim 22 wherein the stent is manufactured from a resilient material.

24. The system of claim 15 wherein the stent is balloon-expandable.

25. The system of claim 15 wherein the stent is formed by bending a continuous elongated element to define the loops and the elongated elements extending there between.

26. The system of claim 15 further comprising a graft material disposed on the stent.

27. A stent having a collapsed configuration and a deployed configuration comprising:
a first end region opposed to a second end region;
elongated elements arranged in a generally zig-zag fashion between the first end region and the second end region; and
a plurality of loops, each of the plurality of loops formed at an overlying intersection of adjacent elongated elements;
wherein the plurality of loops are in a first twist formation when the stent is in the collapsed configuration.

28. A stent comprising:
a first end region at a first longitudinal end of the stent opposed to a second end region at a second longitudinal end of the stent;
elongated elements arranged in a generally zig-zag fashion between the first end region and the second end region; and
a plurality of loops, each of the plurality of loops formed at an overlying intersection of adjacent elongated elements, each of the plurality of loops having a tip;

wherein the tips of the plurality of loops in the first end region form a first end circle, and each individual loop in the first end region is arranged at a twist angle, the twist angle of each individual loop measured in a first end plane defined by the first end circle between a line tangent to the first end circle and intersecting a tip of the individual loop being measured and a loop line longitudinally dividing the individual loop in the first end region; and wherein the twist angle of each individual loop is a first twist angle when the stent is in a collapsed configuration and a second twist angle different from said first twist angle when the stent is in a deployed configuration.

29. The stent of claim 28 wherein the second twist angle is about 45 degrees.

30. The stent of claim 28 wherein the first twist angle is between about 5 to 85 degrees.

31. The stent of claim 28 wherein the tips of the plurality of loops in the second end region form a second end circle, and each individual loop in the second end region is arranged at a twist angle, the twist angle of each individual loop measured in a second end plane defined by the second end circle between a line tangent to the second end circle perpendicular to a radius line from a longitudinal axis of the stent to a tip of the individual loop being measured and a loop line longitudinally dividing the individual loop in the second end region.

32. The stent of claim 28 wherein the overlying intersections for each of the elongated elements are in a same-sided configuration.

33. The stent of claim 28 wherein the overlying intersections for each of the elongated elements are in a over-under configuration.

34. The stent of claim 28 wherein the elongated elements extend generally linearly between opposed loops.

35. The stent of claim 28 wherein the plurality of loops in the first end region is arranged so that one loop contacts an adjacent loop when the stent is in a collapsed configuration.

36. The stent of claim 28 wherein the elongated elements are in physical contact at the overlying intersection of adjacent elongated elements.

37. The stent of claim 28 wherein the stent is self-expanding.

38. The stent of claim 37 wherein the stent is manufactured from a resilient material.

39. The stent of claim 28 wherein the stent is balloon-expandable.

40. The stent of claim 28 wherein the stent is formed by bending a continuous elongated element to define the loops and the elongated elements extending therebetween.

41. The stent of claim 28 further comprising a graft material disposed on the stent.

* * * * *

UNITED STATES PATENT AND TRADEMARK OFFICE
CERTIFICATE OF CORRECTION

| | |
|---|---|
| PATENT NO. | : 6,966,923 B2 |
| APPLICATION NO. | : 10/350582 |
| DATED | : November 22, 2005 |
| INVENTOR(S) | : Darin C. Gittings |

It is certified that error appears in the above-identified patent and that said Letters Patent is hereby corrected as shown below:

Column 9, line 55, " when the stent is in the collapsed configureation." should be changed to --when the stent is in the collapsed configuration and in a second twist formation when the stent is in the deployed configuration.--

Column 10, line 34, "32. The stent of claim 28 wherein the overlying intersect-" should be changed to -- 32. The stent of claim 31 wherein the overlying intersect- --

Column 10, line 37, "33. The stent of claim 28 wherein the overlying intersect-" should be changed to --33. The sent of claim 31 wherein the overlying intersect- --

Signed and Sealed this

Twenty-third Day of October, 2007

JON W. DUDAS
*Director of the United States Patent and Trademark Office*